US012804321B2

(12) United States Patent
Kawamura et al.

(10) Patent No.: US 12,804,321 B2
(45) Date of Patent: Nov. 17, 2026

(54) ACOUSTIC DEVICE

(71) Applicant: Panasonic Intellectual Property Corporation of America, Torrance, CA (US)

(72) Inventors: Akihisa Kawamura, Osaka (JP); Satoshi Takayama, Mie (JP); Takeshi Sakai, Hyogo (JP)

(73) Assignee: PANASONIC INTELLECTUAL PROPERTY CORPORATION OF AMERICA, Torrance, CA (US)

( * ) Notice: Subject to any disclaimer, the term of this patent is extended or adjusted under 35 U.S.C. 154(b) by 158 days.

(21) Appl. No.: 18/531,877

(22) Filed: Dec. 7, 2023

(65) Prior Publication Data

US 2024/0147154 A1 May 2, 2024

Related U.S. Application Data

(63) Continuation of application No. PCT/JP2022/022251, filed on Jun. 1, 2022.

(30) Foreign Application Priority Data

Jun. 16, 2021 (JP) ................................ 2021-100440

(51) Int. Cl.
*H04R 1/28* (2006.01)
*H04R 1/40* (2006.01)
(Continued)

(52) U.S. Cl.
CPC ............... *H04R 3/12* (2013.01); *H04R 1/288* (2013.01); *H04R 1/403* (2013.01); *A61B 5/024* (2013.01);
(Continued)

(58) Field of Classification Search
CPC .... H04R 3/12; H04R 2201/401; H04R 1/288; H04R 1/403; H04R 1/025; H04R 1/02; H04R 1/2819; H04R 1/28; H04R 2201/02
See application file for complete search history.

(56) References Cited

U.S. PATENT DOCUMENTS 4,440,443 A * 4/1984 Nordskog ................ A47C 7/38 297/217.4
5,684,879 A * 11/1997 Verdick .................... H04R 5/02 381/370
(Continued)

FOREIGN PATENT DOCUMENTS

JP 57-196298 12/1982
JP 1-161654 11/1989
(Continued)

OTHER PUBLICATIONS

International Search Report issued Jul. 19, 2022 in International (PCT) Application No. PCT/JP2022/022251.

*Primary Examiner* — Disler Paul
(74) *Attorney, Agent, or Firm* — Wenderoth, Lind & Ponack, L.L.P.

(57) ABSTRACT

An acoustic device includes a first acoustic unit and a second acoustic unit. The first acoustic unit includes: a first loudspeaker module that includes a first sound emitting surface provided to face the second acoustic unit; and a first sound absorbing module that includes a first sound absorbing surface provided around the first sound emitting surface to face the second acoustic unit. The second acoustic unit includes: a second loudspeaker module that includes a second sound emitting surface provided to face the first acoustic unit; and a second sound absorbing module that includes a second sound absorbing surface provided around the second sound emitting surface to face the first acoustic unit.

12 Claims, 9 Drawing Sheets

(51) Int. Cl.
*H04R 3/12* (2006.01)
*A61B 5/024* (2006.01)
*A61B 5/374* (2021.01)

(52) U.S. Cl.
CPC ................ *A61B 5/374* (2021.01); *H04R 1/28* (2013.01); *H04R 2201/401* (2013.01)

(56) References Cited

U.S. PATENT DOCUMENTS

| | | | | |
|---|---|---|---|---|
| 6,744,898 | B1 * | 6/2004 | Hirano | H04R 5/023 381/301 |
| 8,553,890 | B2 * | 10/2013 | Yokota | H04R 5/023 381/1 |
| 9,950,793 | B2 * | 4/2018 | Tracy | H04R 5/023 |
| 10,165,354 | B1 | 12/2018 | Toda et al. | |
| 10,672,377 | B2 * | 6/2020 | Griffin | G10K 11/17854 |
| 10,741,166 | B2 * | 8/2020 | Dyreby | G10K 11/20 |
| 11,223,903 | B2 * | 1/2022 | Guerrini | H04S 7/30 |
| 11,699,427 | B2 * | 7/2023 | Vandijck | H04R 1/345 181/175 |
| 11,950,047 | B2 * | 4/2024 | Corynen | H04R 1/028 |
| 12,073,817 | B2 * | 8/2024 | Tomimatsu | G10K 11/172 |
| 2007/0272482 | A1 | 11/2007 | Yamaguchi et al. | |
| 2008/0175426 | A1 * | 7/2008 | Jacobs | B60R 11/0217 381/376 |
| 2011/0235832 | A1 | 9/2011 | Riopel | |
| 2014/0254831 | A1 * | 9/2014 | Patton | G10H 1/46 381/107 |
| 2019/0280890 | A1 | 9/2019 | Muta et al. | |
| 2021/0074258 | A1 | 3/2021 | Konno et al. | |
| 2021/0227311 | A1 * | 7/2021 | Minarsch | H04R 1/1041 |
| 2024/0348956 | A1 * | 10/2024 | Ito | H04R 1/025 |

FOREIGN PATENT DOCUMENTS

| | | |
|---|---|---|
| JP | 5-344584 | 12/1993 |
| JP | 2005-58287 | 3/2005 |
| JP | 2005-80756 | 3/2005 |
| JP | 2005-338795 | 12/2005 |
| JP | 2009-199383 | 9/2009 |
| JP | 2009-227227 | 10/2009 |
| JP | 2012-502513 | 1/2012 |
| JP | 2019-6191 | 1/2019 |
| JP | 2019-151290 | 9/2019 |
| JP | 2019-212940 | 12/2019 |

* cited by examiner

ACOUSTIC DEVICE

CROSS REFERENCE TO RELATED APPLICATIONS

This is a continuation application of PCT International Application No. PCT/JP2022/022251 filed on Jun. 1, 2022, designating the United Conditions of America, which is based on and claims priority of Japanese Patent Application No. 2021-100440 filed on Jun. 16, 2021. The entire disclosures of the above-identified applications, including the specifications, drawings and claims are incorporated herein by reference in their entirety.

FIELD

The present disclosure relates to an acoustic device provided in a vicinity of the head of a user.

BACKGROUND

With spread of telework in recent years, online conferences such as video conferences or web conferences are actively held in conference spaces simply separated by partitions on office floors, and living rooms at home, for example. In such an online conference, for example, a terminal device that can be connected to the Internet, and a microphone and a loudspeaker connected to the terminal device are used. The terminal device and the microphone are placed on a table, and a user sits on a seat in front of the table. The loudspeaker is mounted on an acoustic device arranged in a headrest of the seat (see Patent Literature (PTL) 1, for example).

Voice uttered by a user is picked up by the microphone placed on the table and delivered to the other party of the online conference. Voice uttered by the other party of the online conference is output from the loudspeaker of the acoustic device, which is mounted on the headrest, and delivered to the user.

CITATION LIST

Patent Literature

PTL 1: Japanese Unexamined Patent Application Publication No. 2005-58287

SUMMARY

Technical Problem

However, with the above-described conventional acoustic device, ambient noise enters the ears of a user, making it difficult for the user to hear sound output from the loudspeaker. In connection with this, when the user raises the volume of the loudspeaker, the sound output from the loudspeaker leaks to the surroundings, causing annoyance to people around the user. In addition, the voice uttered by the user is also leaked to the surroundings, causing annoyance to people around the user.

In view of the above, the present disclosure provides an acoustic device that can a) prevent ambient noise from entering the ears of a user, b) make the sound output from the loudspeaker easy to hear even if the volume of the loudspeaker is reduced, preventing leakage of the sound to the surroundings, and c) prevent the leakage of the sound uttered by the user to the surroundings.

Solution to Problem

An acoustic device according to an aspect of the present disclosure is an acoustic device that is provided in a vicinity of a head of a user, the acoustic device including: a first acoustic unit provided to face a right side of the head of the user; and a second acoustic unit provided to face a left side of the head of the user, in which the first acoustic unit includes: a first loudspeaker module that includes a first sound emitting surface provided to face the second acoustic unit; and a first sound absorbing module that includes a first sound absorbing surface provided around the first sound emitting surface to face the second acoustic unit, and the second acoustic unit includes: a second loudspeaker module that includes a second sound emitting surface provided to face the first acoustic unit; and a second sound absorbing module that includes a second sound absorbing surface provided around the second sound emitting surface to face the first acoustic unit.

These general and specific aspects may be implemented using a system, a method, an integrated circuit, a computer program, or a computer-readable recording medium such as a compact disc-read only memory (CD-ROM), or any combination of systems, methods, integrated circuits, computer programs, or computer-readable recording media.

Advantageous Effects

According to an acoustic device in an aspect of the present disclosure, a) ambient noise can be prevented from entering the ears of a user, b) sound output from a loudspeaker can be made easy to hear even if a volume of the loudspeaker is reduced, preventing leakage of the sound to surroundings, and c) voice uttered by the user can be prevented from leaking to the surroundings.

BRIEF DESCRIPTION OF DRAWINGS

These and other advantages and features will become apparent from the following description thereof taken in conjunction with the accompanying Drawings, by way of non-limiting examples of embodiments disclosed herein.

DESCRIPTION OF EMBODIMENTS

Figure 1:
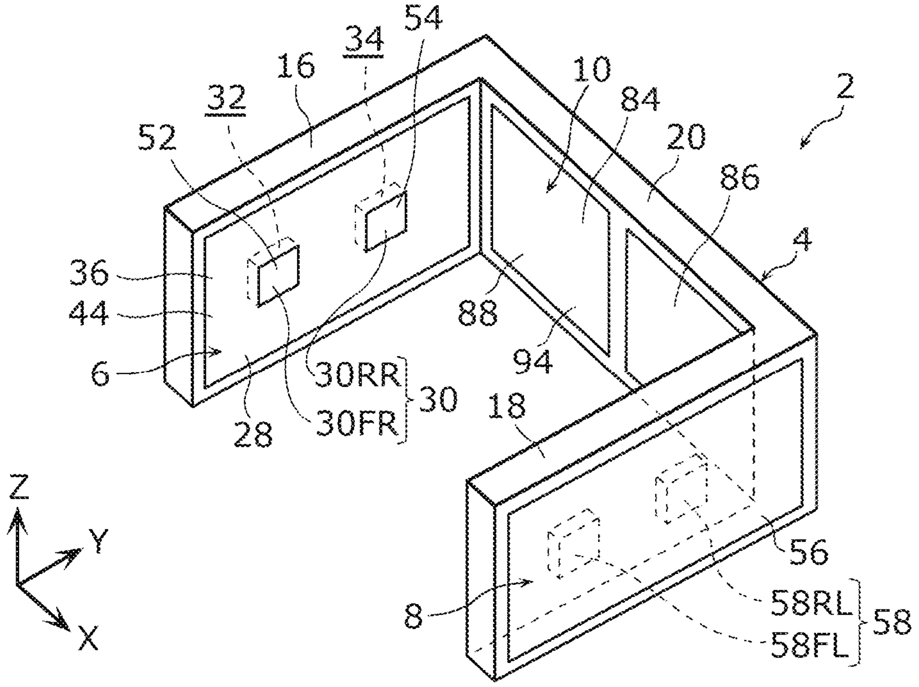
FIG. 1 is a perspective view showing an acoustic device according to Embodiment 1.

An acoustic device according to an aspect of the present disclosure is an acoustic device that is provided in a vicinity of a head of a user, the acoustic device including: a first acoustic unit provided to face a right side of the head of the user; and a second acoustic unit provided to face a left side of the head of the user, in which the first acoustic unit includes: a first loudspeaker module that includes a first sound emitting surface provided to face the second acoustic unit; and a first sound absorbing module that includes a first sound absorbing surface provided around the first sound emitting surface to face the second acoustic unit, and the second acoustic unit includes: a second loudspeaker module that includes a second sound emitting surface provided to face the first acoustic unit; and a second sound absorbing module that includes a second sound absorbing surface provided around the second sound emitting surface to face the first acoustic unit.

According to the present aspect, the first acoustic unit and the second acoustic unit are respectively arranged to face the right side and left side of the user's head. With this configuration, a part of the voice uttered by the user is absorbed by the first sound absorbing module and/or the second sound absorbing module, so that the voice uttered by the user can be prevented from leaking to the surroundings. As a result, it is possible to prevent people around the user from feeling that the voice uttered by the user is annoying. In addition, since ambient noise is absorbed by the first sound absorbing module and/or the second sound absorbing module, it is possible to prevent the ambient noise from entering the ears of the user. Accordingly, the user can easily hear the sound output from each of the first loudspeaker module and the second loudspeaker module. In relation to this, even if the volume of each of the first loudspeaker module and the second loudspeaker module is reduced, the user can easily hear the sound output from each of the first loudspeaker module and the second loudspeaker module, and leakage of the sound to the surroundings can be prevented. As a result, it is possible to prevent people around the user from feeling that the sound output from each of the first loudspeaker module and the second loudspeaker module is annoying.

For example, each of the first sound absorbing module and the second sound absorbing module may be a sound absorbing element capable of absorbing sound with one or more sound absorption frequencies.

According to the present aspect, a desired sound (for example, ambient noise or the voice uttered by a user, or the like) can be absorbed by the first sound absorbing module and the second sound absorbing module by selecting the sound absorption frequency of each of the first sound absorbing module and the second sound absorbing module according to usage of the acoustic device.

For example, the first acoustic unit may include a plurality of the first loudspeaker modules, and the second acoustic unit may include a plurality of the second loudspeaker modules.

According to the present aspect, the directivity of the sound output from each of the plurality of first loudspeaker modules can be controlled by adjusting positional relationship of the plurality of first loudspeaker modules. Furthermore, the directivity of the sound output from each of the plurality of second loudspeaker modules can be controlled by adjusting positional relationship of the plurality of second loudspeaker modules.

For example, the first loudspeaker module may include: a first loudspeaker that includes the first sound emitting surface; and a first directivity control member provided to face the first sound emitting surface of the first loudspeaker, for controlling directivity of sound output from the first sound emitting surface, and the second loudspeaker module may include: a second loudspeaker that includes the second sound emitting surface; and a second directivity control member provided to face the second sound emitting surface of the second loudspeaker, for controlling directivity of sound output from the second sound emitting surface.

According to the present aspect, the directivity of the sound output from the first sound emitting surface of the first loudspeaker can be controlled by the first directivity control member. The directivity of the sound output from the second sound emitting surface of the second loudspeaker can also be controlled by the second directivity control member.

For example, each of the first directivity control member and the second directivity control member may be an acoustic lens or a horn.

According to the present aspect, it is possible to easily control the directivity of the sound output from each of the first sound emitting surface and the second sound emitting surface.

For example, a reproduction band of the first loudspeaker module is (i) an audible sound range that is humanly recognizable, the audible sound range being a low sound range or a medium-high sound range, or (ii) a non-audible sound range that is not humanly recognizable, and a reproduction band of the second loudspeaker module is (i) an audible sound range that is humanly recognizable, the audible sound range being a low sound range or a medium-high sound range, or (ii) a non-audible sound range that is not humanly recognizable.

According to the present aspect, it is possible to appropriately set the reproduction band of each of the first loudspeaker module and the second loudspeaker module, according to the usage of the acoustic device.

For example, the first sound emitting surface of the first loudspeaker module and the first sound absorbing surface of the first sound absorbing module may be arranged substantially parallel to each other, and the second sound emitting surface of the second loudspeaker module and the second sound absorbing surface of the second sound absorbing module may be arranged substantially parallel to each other.

According to the present aspect, it is possible to prevent the sound output from the first sound emitting surface of the first loudspeaker module from being absorbed by the first sound absorbing surface of the first sound absorbing module. As a result, the sound output from the first sound emitting surface of the first loudspeaker module can be efficiently delivered to the right ear of a user. In addition, it is possible to prevent the sound output from the second sound emitting surface of the second loudspeaker module from being absorbed by the second sound absorbing surface of the second sound absorbing module. As a result, the sound output from the second sound emitting surface of the second loudspeaker module can be efficiently delivered to the left ear of a user.

For example, the acoustic device may further include a controller that switches to one mode among a plurality of modes having mutually different acoustic characteristics, and controls sound output from each of the first loudspeaker module and the second loudspeaker module, according to the one mode switched to.

According to the present aspect, it is possible to switch to any mode from a plurality of modes.

For example, the acoustic device may further include: an action schedule data obtainer that obtains action schedule data indicating an action schedule of the user, and the controller may switch to, among the plurality of modes, a mode corresponding to the action schedule data obtained by the action schedule data obtainer.

According to the present aspect, it is possible to switch to an optimum mode from the plurality of modes, according to the action schedule data.

For example, the acoustic device may further include a vital data obtainer that obtains vital data of the user; and an estimator that estimates a condition of the user based on the vital data obtained by the vital data obtainer, and the controller may switch to, among the plurality of modes, a mode corresponding to the condition of the user estimated by the estimator.

According to the present aspect, it is possible to switch to the optimum mode from the plurality of modes, according to the condition of the user.

For example, the acoustic device may further include a third acoustic unit provided to face a back side of the head of the user, and the third acoustic unit may include a third sound absorbing module that includes a third sound absorbing surface provided to face a space between the first acoustic unit and the second acoustic unit.

According to the present aspect, the first acoustic unit, the second acoustic unit, and the third acoustic unit are respectively arranged to face the right side, left side, back side of the user's head. With this configuration, a part of the voice uttered by the user is absorbed by the first sound absorbing module, the second sound absorbing module, and/or the third sound absorbing module, so that the voice uttered by the user can be effectively prevented from leaking to the surroundings. In addition, since ambient noise is absorbed by the first sound absorbing module, the second sound absorbing module, and/or the third sound absorbing module, it is possible to prevent the ambient noise from entering the ear of a user, more effectively.

For example, the third acoustic unit may further include a third loudspeaker module that includes a third sound emitting surface provided to face the space, and the third sound absorbing surface of the third sound absorbing module may be provided around the third sound emitting surface of the third loudspeaker module.

According to this aspect, a desired sound field can be easily formed in a space surrounded by the first acoustic unit, the second acoustic unit, and the third acoustic unit by outputting sound from each of the first loudspeaker module, the second loudspeaker module, and the third loudspeaker module.

These general and specific aspects may be implemented using a system, a method, an integrated circuit, a computer program, or a computer-readable recording medium such as a CD-ROM, or any combination of systems, methods, integrated circuits, computer programs, or computer-readable recording media.

Hereinafter, embodiments are specifically described, with reference to the drawings.

Each of the exemplary embodiments described below shows a general or specific example. The numerical values, shapes, materials, elements, the arrangement and connection of the elements, steps, the processing order of the steps etc. shown in the following exemplary embodiments are mere examples, and therefore do not limit the scope of the appended claims and their equivalents. Therefore, among the elements in the following exemplary embodiments, those not recited in any one of the independent claims are described as optional elements.

Embodiment 1

[1-1. Configuration of Acoustic Device]

Figure 2:
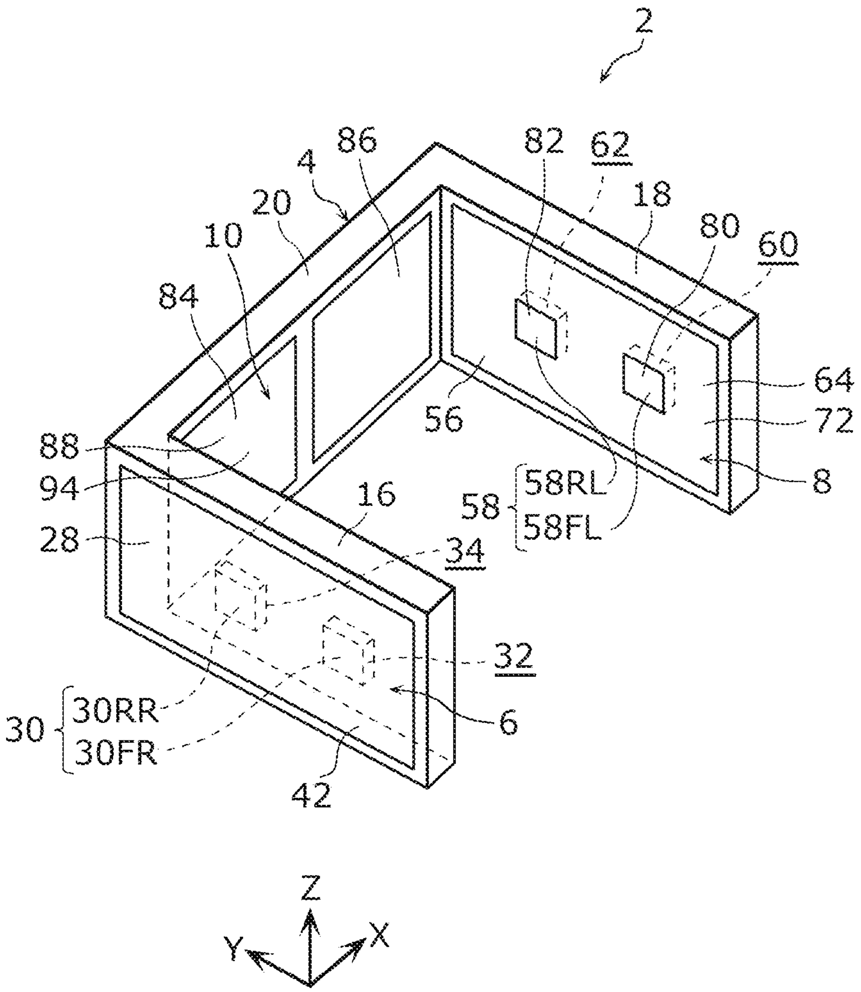
FIG. 2 is a perspective view showing the acoustic device according to Embodiment 1, viewed from a direction different from a viewing direction in FIG. 1.
Figure 3:
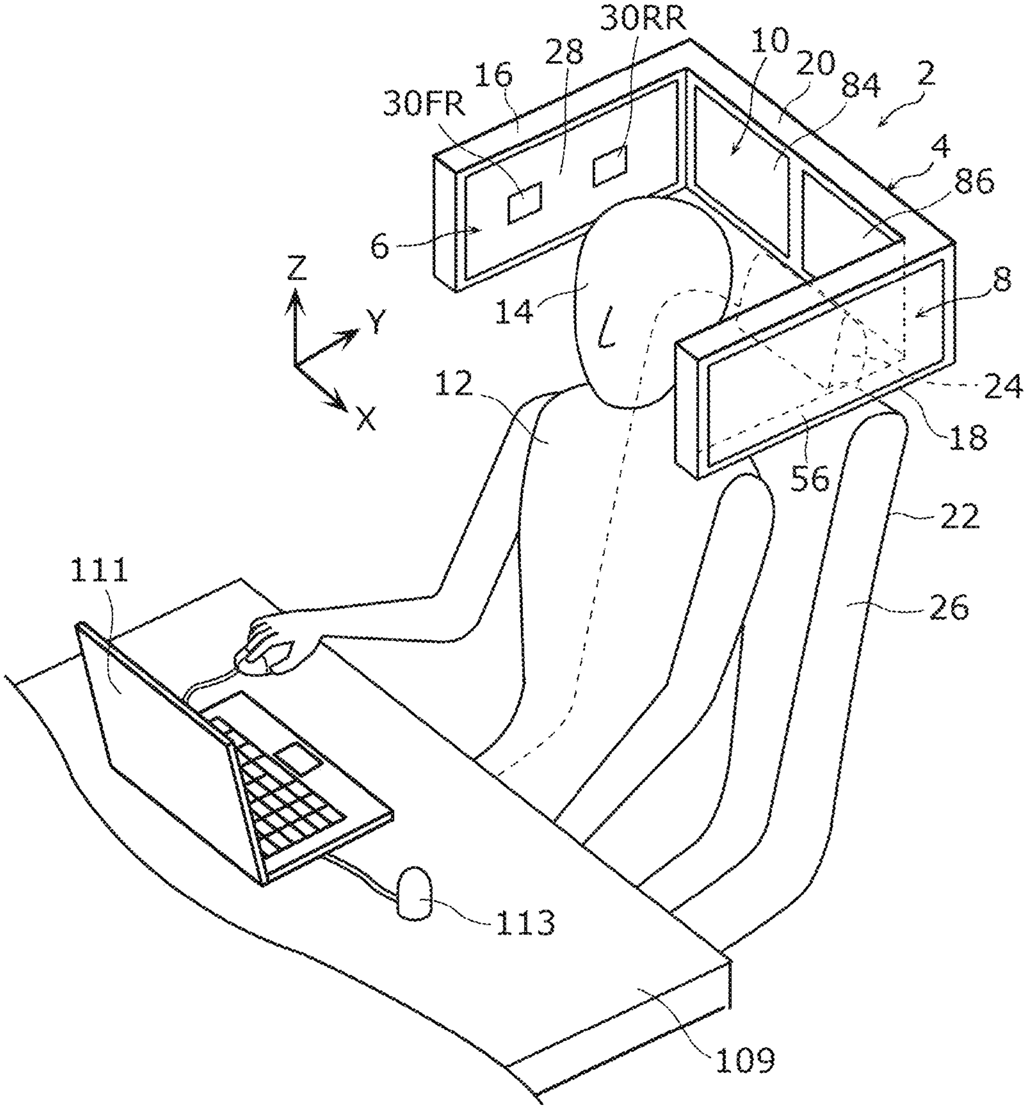
FIG. 3 is a perspective view showing a usage example of the acoustic device according to Embodiment 1.
Figure 4:
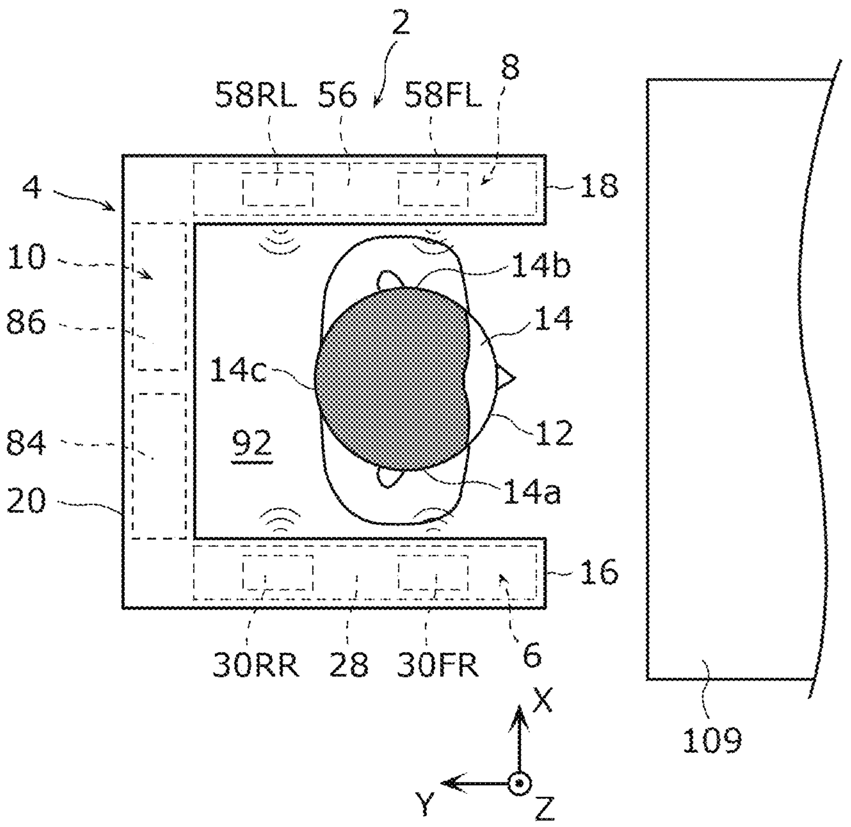
FIG. 4 is a plan view showing a usage example of the acoustic device according to Embodiment 1.
Figure 5:
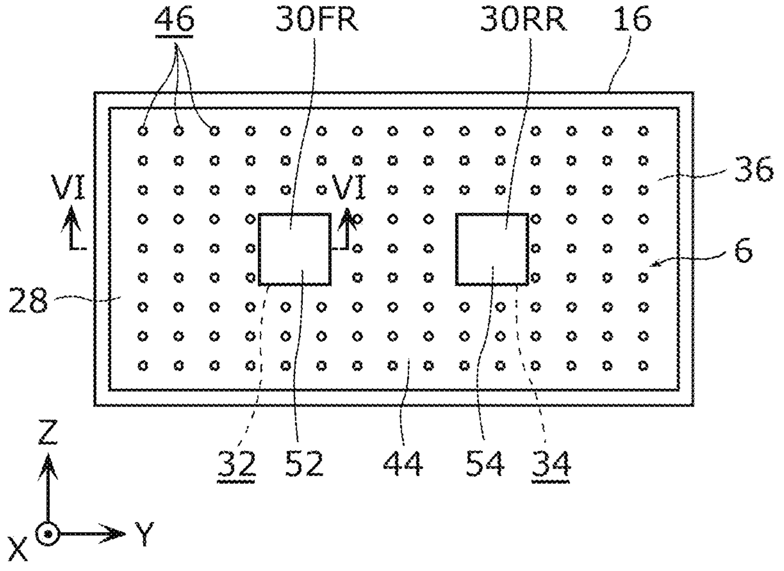
FIG. 5 is a diagram showing a first acoustic unit according to Embodiment 1.
Figure 6:
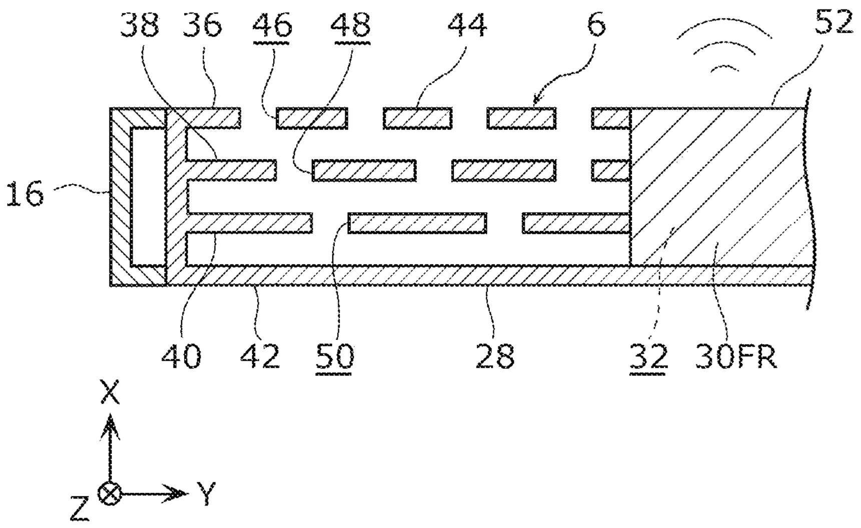
FIG. 6 is a cross-sectional view of a main part of the first acoustic unit according to Embodiment 1, taken along the line VI-VI in FIG. 5.
Figure 7:
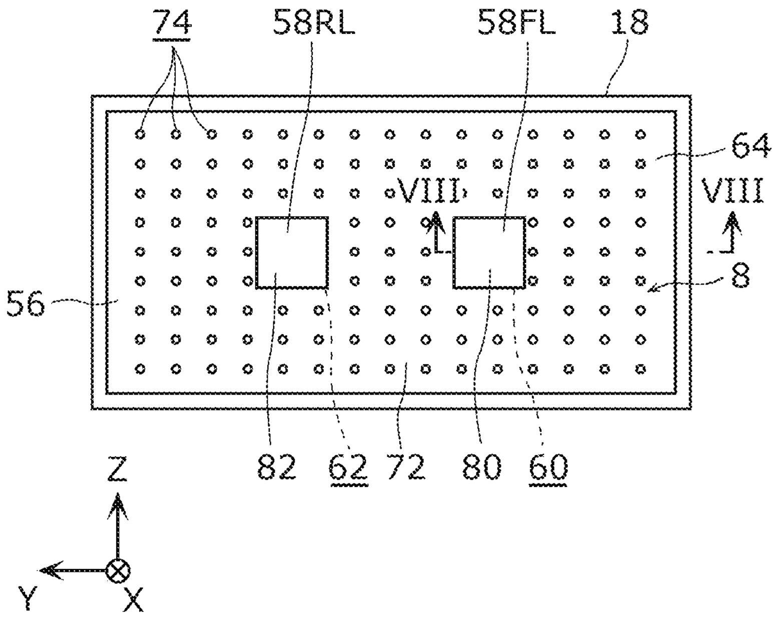
FIG. 7 is a diagram showing a second acoustic unit according to Embodiment 1.
Figure 8:
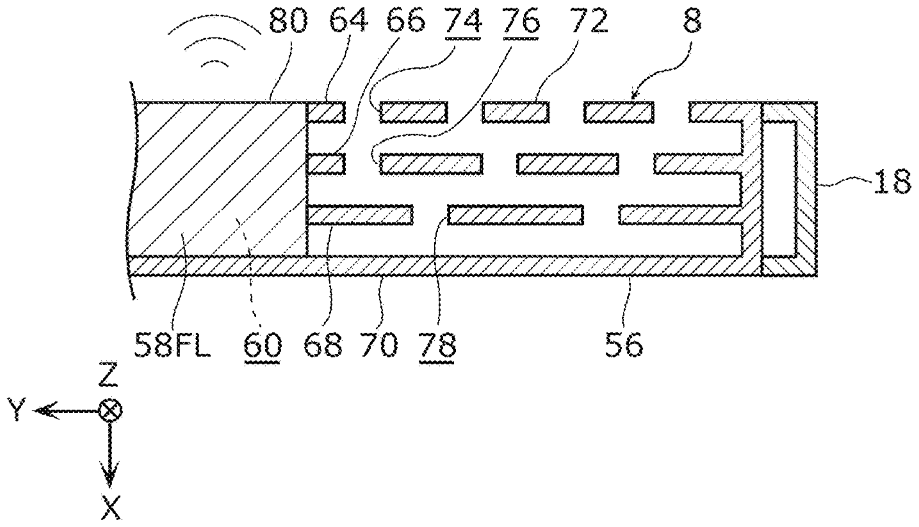
FIG. 8 is a cross-sectional view of a main part of the second acoustic unit according to Embodiment 1, taken along the line VIII-VIII in FIG. 7.
Figure 9:
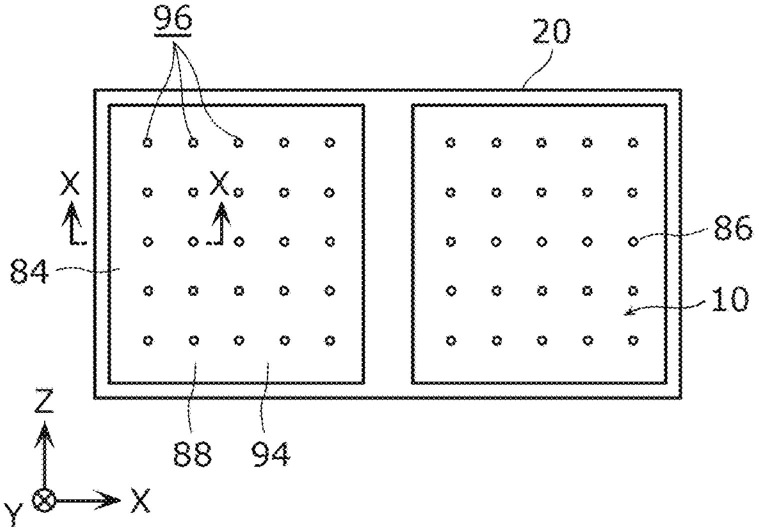
FIG. 9 is a diagram showing a third acoustic unit according to Embodiment 1.
Figure 10:
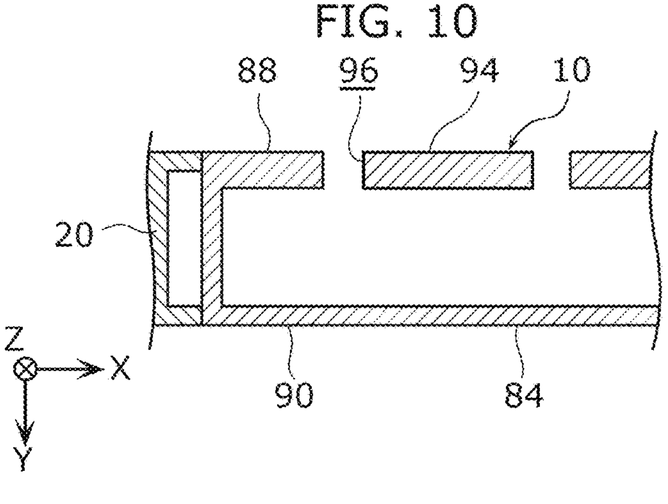
FIG. 10 is a cross-sectional view of a main part of the third acoustic unit according to Embodiment 1, taken along the line X-X in FIG. 9.

First, a configuration of acoustic device 2 according to Embodiment 1 will be described with reference to FIGS. 1 to 10. FIG. 1 is a perspective view showing acoustic device 2 according to Embodiment 1. FIG. 2 is a perspective view showing acoustic device 2 according to Embodiment 1, viewed from a direction different from a viewing direction of FIG. 1. FIG. 3 is a perspective view showing a usage example of acoustic device 2 according to Embodiment 1. FIG. 4 is a plan view showing a usage example of acoustic device 2 according to Embodiment 1. FIG. 5 is a diagram showing first acoustic unit 6 according to Embodiment 1. FIG. 6 is a cross-sectional view of a main part of first acoustic unit 6 according to Embodiment 1, taken along the line VI-VI in FIG. 5. FIG. 7 is a diagram showing second acoustic unit 8 according to Embodiment 1. FIG. 8 is a cross-sectional view of a main part of second acoustic unit 8 according to Embodiment 1, taken along the line VIII-VIII in FIG. 7. FIG. 9 is a diagram showing third acoustic unit 10 according to Embodiment 1. FIG. 10 is a cross-sectional view of a main part of third acoustic unit 10 according to Embodiment 1, taken along the line X-X in FIG. 9.

In FIGS. 1 to 10, the left-right direction of acoustic device 2 is an X-axis direction, the front-rear direction of acoustic device 2 is a Y-axis direction, and the vertical direction of acoustic device 2 is a Z-axis direction.

As shown in FIGS. 1 and 2, acoustic device 2 includes housing 4, first acoustic unit 6, second acoustic unit 8, and third acoustic unit 10. As shown in FIG. 3, acoustic device 2 is a headrest-type acoustic device provided in a vicinity of head 14 of user 12, and includes, for example, a four-channel loudspeaker unit (described later) that outputs sound toward head 14 of user 12.

Housing 4 is a member for supporting first acoustic unit 6, second acoustic unit 8, and third acoustic unit 10. Housing 4 has first support portion 16, second support portion 18, and third support portion 20. Each of first support portion 16, second support portion 18, and third support portion 20 is formed in a rectangular frame shape. First support portion 16 and second support portion 18 are spaced apart in the left-right direction (X-axis direction) and are arranged substantially parallel to each other. Third support portion is arranged to connect one end portion of first support portion 16 in the front-rear direction (Y-axis direction) and one end portion of second support portion 18 in the front-rear direction. In other words, housing 4 is formed in a U shape (substantially U shape) in an XY plan view.

As shown in FIG. 3, housing 4 is supported by headrest 24 of seat 22 on which user 12 sits. It should be noted that headrest 24 is arranged at the upper end portion of backrest portion 26 of seat 22. As shown in FIGS. 3 and 4, first support portion 16, second support portion 18, and third support portion 20 of housing 4 are arranged to surround head 14 of user 12 seated on seat 22, from three sides. Specifically, first support portion 16, second support portion 18, and third support portion 20 of housing 4 respectively arranged to face right-side head part 14*a*, left-side head part 14*b*, and back-side head part 14*c* of user 12 seated on seat 22.

First acoustic unit 6 is supported by first support portion 16 of housing 4 and arranged to face right-side head part 14*a* of user 12 seated on seat 22. Second acoustic unit 8 is supported by second support portion 18 of housing 4 and arranged to face left-side head part 14*b* of user 12 seated on seat 22. Third acoustic unit 10 is supported by third support portion 20 of housing 4 and arranged to face back-side head part 14*c* of user 12 seated on seat 22. Each configuration of first acoustic unit 6, second acoustic unit 8, and third acoustic unit 10 will be described below.

As shown in FIGS. 1, 4 and 5, first acoustic unit 6 has first sound absorbing module 28 and a pair of first loudspeaker modules 30.

First sound absorbing module 28 is a resonance type sound absorbing element that attenuates sound energy to obtain a sound absorbing effect, and is, for example, a three-layer type Helmholtz resonator capable of absorbing sound with sound absorption frequencies (center frequencies) of 3 kHz, 4 kHz and 5 kHz. Here, the three-layer type Helmholtz resonator absorbs sound (for example, harsh sound such as ambient noise) in a frequency band (3 kHz to 5 kHz) to which human hearing is highly sensitive. In this embodiment, sound absorption frequencies of first sound absorbing module 28 are 3 kHz, 4 kHz, and 5 kHz, but the sound absorption frequencies are not limited to these frequencies, and the sound absorption frequencies can be selectively determined according to the application of acoustic device 2. As shown in FIG. 5, first sound absorbing module 28 is formed in a rectangular panel shape as viewed from a YZ plane. A pair of recesses 32 and 34 are formed in first sound absorbing module 28. The pair of recesses 32 and 34 are spaced apart in the front-rear direction.

As shown in FIG. 6, first sound absorbing module 28 has first layer 36, second layer 38, third layer 40, and base layer 42, and each of layers 36, 38, 40, and 42 is formed in a thin plate shape. Each thickness of first layer 36, second layer 38, and third layer 40 is 1 mm, for example. First layer 36, second layer 38, third layer 40, and base layer 42 are spaced apart in this order in a direction along the thickness of first sound absorbing module 28 (X-axis direction). First layer 36 is located on a side closer to second acoustic unit 8, and base layer 42 is located on a side far from second acoustic unit 8. First sound absorbing surface 44 is formed on a surface of first layer 36 on the side facing second acoustic unit 8. First sound absorbing surface 44 is arranged to face second acoustic unit 8. A distance between first layer 36 and second layer 38, a distance between second layer 38 and third layer 40, and a distance between third layer 40 and base layer 42 are all 10 mm, for example.

As shown in FIGS. 5 and 6, first layer 36 has a plurality of circular holes 46 formed therein. A plurality of holes 46 in first layer 36 are arranged in a grid. Second layer 38 has a plurality of circular holes 48 formed therein. A plurality of holes 48 in second layer 38 are arranged in a grid. Third layer 40 have a plurality of circular holes 50 formed therein. A plurality of holes 50 in third layer 40 are arranged in a grid. Base layer 42 does not have a plurality of holes formed therein. For convenience of explanation, in FIGS. 1 and 3, illustration of a plurality of holes 46 in first layer 36 is omitted.

The diameters of each hole 46 in first layer 36, each hole 48 in second layer 38 and each hole 50 in third layer 40 are 5 mm, for example. A pitch of holes 46 in first layer 36 (the pitch in the Y-axis direction and the Z-axis direction) is 9.6 mm, for example. The pitch of holes 48 in second layer 38 is 12 mm, for example. The pitch of holes 50 in third layer 40 is 16 mm, for example.

A pair of first loudspeaker modules 30 respectively include right front loudspeaker 30FR (an example of a first loudspeaker) and right rear loudspeaker 30RR (an example of the first loudspeaker), which constitute a four-channel loudspeaker unit. A reproduction band of each of right front loudspeaker 30FR and right rear loudspeaker 30RR is a low sound range or a medium-high sound range, which is an audible range that can be recognized by humans. Right front loudspeaker 30FR and right rear loudspeaker 30RR are respectively arranged in a pair of recesses 32 and 34 formed in first sound absorbing module 28. With this configuration, right front loudspeaker 30FR and right rear loudspeaker 30RR are spaced apart in the front-rear direction. Right rear loudspeaker 30RR is arranged closer to third acoustic unit 10 than right front loudspeaker 30FR. Right front loudspeaker 30FR and right rear loudspeaker 30RR are arranged so as to form directivity at or near the right ear of user 12.

Right front loudspeaker 30FR has first sound emitting surface 52 for outputting sound. Right rear loudspeaker 30RR has first sound emitting surface 54 for outputting sound. These first sound emitting surfaces 52 and 54 are arranged to face second acoustic unit 8. First sound absorbing surface 44 of first sound absorbing module 28 is arranged around first sound emitting surfaces 52 and 54. In the present specification, "arranged around" shall mean not only an arrangement of all-around surrounding, but also an adjacent arrangement. First sound emitting surfaces 52, 54 and first sound absorbing surface 44 of first sound absorbing module 28 are arranged substantially parallel to each other. First sound emitting surfaces 52 and 54 and first sound absorbing surface 44 of first sound absorbing module 28 may be arranged on the same plane.

As shown in FIGS. 2, 7 and 8, second acoustic unit 8 has second sound absorbing module 56 and a pair of second loudspeaker modules 58.

Second sound absorbing module 56 is a resonance-type sound absorbing element that attenuates sound energy to obtain a sound absorbing effect, and is, for example, a three-layer type Helmholtz resonator capable of absorbing sound with absorption frequencies of 3 kHz, 4 kHz and 5 kHz. In the present embodiment, the sound absorption frequencies of second sound absorbing module 56 are 3 kHz, 4 kHz, and 5 kHz, but the sound absorption frequencies are not limited to these frequencies, and can be selectively determined according to the application of acoustic device 2. As shown in FIG. 7, second sound absorbing module 56 is formed in a rectangular panel shape when viewed from a YZ plane. A pair of recesses 60 and 62 are formed in second sound absorbing module 56. The pair of recesses 60 and 62 are spaced apart in the front-rear direction.

As shown in FIG. 8, second sound absorbing module 56 has first layer 64, second layer 66, third layer 68, and base layer 70. Each of layers 64, 66, 68, and 70 is formed in a thin plate shape. Each thickness of first layer 64, second layer 66, and third layer 68 is 1 mm, for example. First layer 64, second layer 66, third layer 68, and base layer 70 are spaced apart in this order in a direction along the thickness of second sound absorbing module 56 (X-axis direction). First layer 64 is located on a side closer to first acoustic unit 6, and base layer 70 is located on a side far from first acoustic unit 6. Second sound absorbing surface 72 is formed on a surface of first layer 64 on the side facing first acoustic unit 6. Second sound absorbing surface 72 is arranged to face first acoustic unit 6. A distance between first layer 64 and second layer 66, a distance between second layer 66 and third layer 68, and a distance between third layer 68 and base layer 70 are all 10 mm, for example.

As shown in FIGS. 7 and 8, first layer 64 has a plurality of circular holes 74 formed therein. A plurality of holes 74 in first layer 64 are arranged in a grid. Second layer 66 has a plurality of circular holes 76 formed therein. A plurality of holes 76 in second layer 66 are arranged in a grid. Third layer 68 has a plurality of circular holes 78 formed therein. A plurality of holes 78 in third layer 68 are arranged in a grid. Base layer 70 does not have a plurality of holes formed therein. For convenience of explanation, in FIG. 2, illustration of a plurality of holes 74 in first layer 64 is omitted.

The diameters of each hole 74 in first layer 64, each hole 76 in second layer 66, and each hole 78 in third layer 68 are 5 mm, for example. The pitch of holes 74 in first layer 64 (the pitch in the Y-axis direction and the Z-axis direction) is 9.6 mm, for example. The pitch of holes 76 in second layer 66 is 12 mm, for example. The pitch of holes 78 in third layer 68 is 16 mm, for example.

A pair of second loudspeaker modules 58 respectively include left front loudspeaker 58FL (an example of a second loudspeaker) and left rear loudspeaker 58RL (an example of the second loudspeaker), which constitute the four-channel loudspeaker unit. A reproduction band of each of left front loudspeaker 58FL and left rear loudspeaker 58RL is a low sound range or a medium-high sound range, which is an audible range that can be recognized by humans. Left front loudspeaker 58FL and left rear loudspeaker 58RL are respectively arranged in a pair of recesses 60 and 62 formed in second sound absorbing module 56. With this configuration, left front loudspeaker 58FL and left rear loudspeaker 58RL are spaced apart in the front-rear direction. Left rear loudspeaker 58RL is arranged closer to third acoustic unit 10 than left front loudspeaker 58FL. Left front loudspeaker 58FL and left rear loudspeaker 58RL are arranged to face right front loudspeaker 30FR and right rear loudspeaker 30RR, respectively. Left front loudspeaker 58FL and left rear loudspeaker 58RL are arranged so as to form directivity at or near the left ear of user 12.

Left front loudspeaker 58FL has second sound emitting surface 80 for outputting sound. Left rear loudspeaker 58RL has second sound emitting surface 82 for outputting sound. These second sound emitting surfaces 80 and 82 are arranged to face first acoustic unit 6. Second sound absorbing surface 72 of second sound absorbing module 56 is arranged around second sound emitting surfaces 80 and 82. Second sound emitting surfaces 80 and 82, and second sound absorbing surface 72 of second sound absorbing module 56 are arranged substantially parallel to each other. Second sound emitting surfaces 80 and 82 and second sound absorbing surface 72 of second sound absorbing module 56 may be arranged on the same plane.

As shown in FIGS. 1, 9 and 10, third acoustic unit 10 includes third sound absorbing modules 84 and 86.

Each of third sound absorbing modules 84 and 86 is a resonance-type sound absorbing element that attenuates sound energy to obtain a sound absorbing effect, and is, for example, one-layer type Helmholtz resonator capable of absorbing sound with a sound absorption frequency of 500 Hz. Here, the one-layer type Helmholtz resonator absorbs sound (for example, human voice in conversation, and the like) in the frequency band (500 Hz to 2 kHz) of the voice uttered by a human. In the present embodiment, the sound absorption frequency of each of third sound absorbing modules 84 and 86 is set to 500 Hz, but is not limited to this frequency. Sound absorption frequency can be selectively determined according to the application of acoustic device 2, for example. As shown in FIG. 9, each of third sound absorbing modules 84 and 86 is formed in a rectangular panel shape, as viewed from an XZ plane. Since configurations of third sound absorbing modules 84 and 86 are the same, only the configuration of third sound absorbing module 84 will be described below.

As shown in FIG. 10, third sound absorbing module 84 has first layer 88 and base layer 90. Each of layers 88 and 90 is formed in a thin plate shape. Thickness of first layer 88 is 3 mm, for example. First layer 88 and base layer 90 are spaced apart in this order in a direction along the thickness of third sound absorbing module 84 (Y-axis direction). First layer 88 is located on the side closer to space 92 (see FIG. 4) between first acoustic unit 6 and second acoustic unit 8, and base layer 90 is located on a side far from space 92. Third sound absorbing surface 94 is formed on a surface of first layer 88 on the side close to space 92. Third sound absorbing surface 94 is arranged to face space 92. A distance between first layer 88 and base layer 90 is 50 mm, for example.

As shown in FIGS. 9 and 10, first layer 88 has a plurality of circular holes 96 formed therein. A plurality of holes 96 in first layer 88 are arranged in a grid. Base layer 90A does not have a plurality of holes formed therein. For convenience of explanation, in FIGS. 1 to 3, illustration of a plurality of holes 96 in first layer 88 is omitted. The diameter of each of holes 96 in first layer 88 is 5 mm, for example. The pitch of holes 96 in first layer 88 (the pitch in the X-axis direction and the Z-axis direction) is 32 mm, for example.

Figure 11:
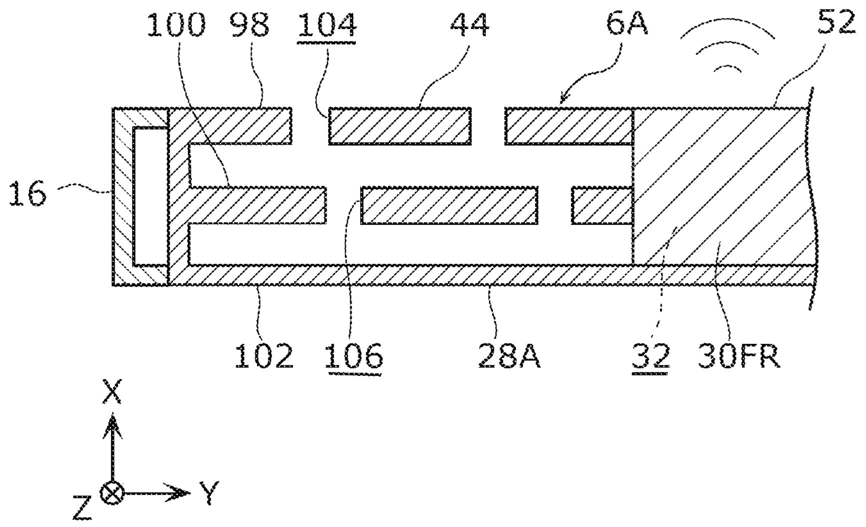
FIG. 11 is a cross-sectional view of a main part of a first acoustic unit according to Variation of Embodiment 1.

In the present embodiment, first sound absorbing module 28 is a one-layer type Helmholtz resonator, but is not limited to this type, and may be a two-layer type Helmholtz resonator, for example. Hereinafter, the configuration of first acoustic unit 6A according to Variation of Embodiment 1 will be described below with reference to FIG. 11. FIG. 11 is a cross-sectional view of a main part of first acoustic unit 6A according to Variation of Embodiment 1. In FIG. 11, the same components as those in FIG. 6 are denoted by the same reference numerals, and descriptions of those components are omitted.

As shown in FIG. 11, first sound absorbing module 28A of first acoustic unit 6A is a resonance-type sound absorbing element that attenuates sound energy to obtain a sound absorbing effect, and is, for example, a two-layer type Helmholtz resonator that is capable of absorbing sound with absorption frequencies of 1 kHz and 2 kHz. Here, the two-layer type Helmholtz resonator absorbs sound (for example, human voice in conversation, and the like) in the frequency band of the voice uttered by a human (500 Hz to 2 kHz).

First sound absorbing module 28A has first layer 98, second layer 100, and base layer 102. Each of layers 98, 100, and 102 is formed in a thin plate shape. Thickness of each of first layer 98 and second layer 100 is 3 mm, for example. First layer 98, second layer 100, and base layer 102 are spaced apart in this order in a direction along the thickness of first sound absorbing module 28A. A distance between first layer 98 and second layer 102 is 20 mm, for example. A distance between second layer 100 and base layer 102 is 30 mm, for example.

As shown in FIG. 11, first layer 98 has a plurality of circular holes 104 formed therein. A plurality of holes 104 in first layer 98 are arranged in a grid. Second layer 100 has a plurality of circular holes 106 formed therein. A plurality of holes 106 in second layer 100 are arranged in a grid. Base layer 102A does not have a plurality of holes formed therein.

The diameters of each hole 104 in first layer 98 and each hole 106 in second layer 100 are 5 mm, for example. The pitch of holes 104 in first layer 98 is 12.6 mm, for example. The pitch of holes 106 in second layer 100 is 20 mm, for example.

Note that each of first sound absorbing module 28, second sound absorbing module 56, and third sound absorbing module 84 may be any type of Helmholtz resonator among one-layer type, two-layer type, or three-layer type Helmholtz resonance according to the application or the like of acoustic device 2.

Furthermore, in the present embodiment, each of first sound absorbing module 28, second sound absorbing module 56, and third sound absorbing module 84 is the resonance-type sound absorbing element, but the present disclosure is not limited to the type. Each of first sound absorbing module 28, second sound absorbing module 56 and third sound absorbing module 84 may be any sound absorbing element among a) a porous sound absorbing element, b) a surface resonance sound absorbing element, and c) the resonance type sound absorbing element.

In addition, in the present embodiment, the reproduction band of each of right front loudspeaker 30FR, right rear loudspeaker 30RR, left front loudspeaker 58FL, and left rear loudspeaker 58RL is set to a low sound range or a medium-high sound range, which is an audible range that can be recognized by humans, but is not limited to the ranges. For example, at least one of the reproduction bands of right front loudspeaker 30FR, right rear loudspeaker 30RR, left front loudspeaker 58FL, and left rear loudspeaker 58RL may be a non-audible sound range (e.g., 40 kHz to 100 kHz) that cannot be recognized by humans. With this configuration, a so-called hypersonic effect can be obtained in which the brain of user 12 is activated and the power of concentration increases.

[1-2. Functional Configuration of Acoustic Device]

Figure 12:
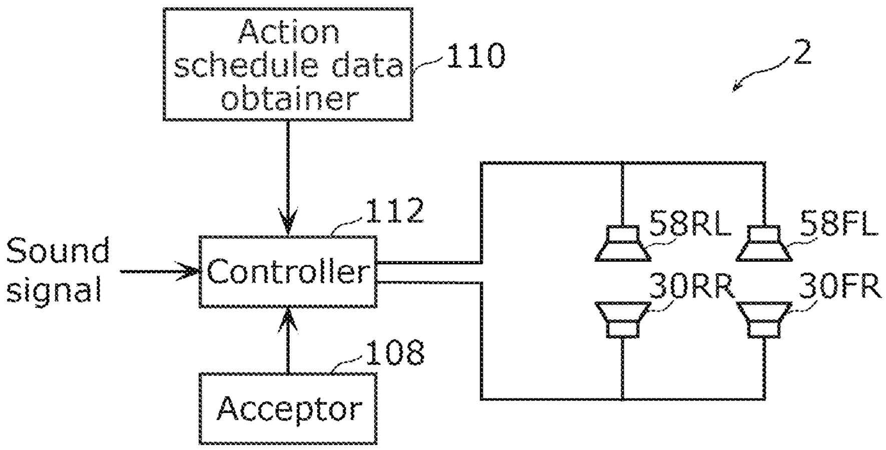
FIG. 12 is a block diagram showing a functional configuration of the acoustic device according to Embodiment 1.

Subsequently, the functional configuration of acoustic device 2 according to Embodiment 1 will be described with reference to FIG. 12. FIG. 12 is a block diagram showing the functional configuration of acoustic device 2 according to Embodiment 1.

As shown in FIG. 12, acoustic device 2 according to Embodiment 1 includes acceptor 108, action schedule data obtainer 110, and controller 112 as functional configurations.

Acceptor 108 is a user interface that accepts an operation by user 12, and is arranged in housing 4 (see FIG. 1), for example. Acceptor 108 accepts an operation by user 12 of selecting one of a plurality of modes having different acoustic characteristics, and outputs, to controller 112, an operation signal indicating the accepted operation from user 12. The plurality of modes include, for example, a conference mode, a concentration mode, and a relax mode.

The conference mode is used when user 12 conducts an online conference such as a video conference or a web conference. In the conference mode, voice of the other party in the online conference can be heard clearly. The concentration mode is used when user 12 wants to concentrate on work or the like. In the concentration mode, ambient noise is canceled to create a quiet environment for user 12. The relax mode used when user 12 wants to relax. In the relax mode, environmental sounds and the like can be heard from all around user 12.

Action schedule data obtainer 110 obtains action schedule data indicating an action schedule of user 12, from terminal device 111 used by user 12. The action schedule data is, for example, managed by a calendar application installed in terminal device 111, and indicates an action schedule such as "web conference from 13:00 to 14:00 on May 31, 2021". Action schedule data obtainer 110 outputs the obtained action schedule data to controller 112.

A sound signal from a sound source is input to controller 112. Controller 112 performs processing on the input sound signal, to thereby control sound output from each of right front loudspeaker 30FR, right rear loudspeaker 30RR, left front loudspeaker 58FL, and left rear loudspeaker 58RL.

Controller 112 switches to one of the plurality of modes described above, based on the operation signal from acceptor 108. For example, when user 12 performs an operation of selecting the conference mode, controller 112 switches to the conference mode from a plurality of modes based on the operation signal from acceptor 108. Based on the switched mode, controller 112 controls sound output from each of right front loudspeaker 30FR, right rear loudspeaker 30RR, left front loudspeaker 58FL, and left rear loudspeaker 58RL.

When switching to the conference mode, for example, controller 112 drives only right front loudspeaker 30FR and left front loudspeaker 58FL. In this case, a sound signal representing the voice of the other party in the online conference is input from terminal device 111 to controller 112. Accordingly, controller 112 performs processing on the input sound signal to cause the voice of the other party in the online conference to be output from each of right front loudspeaker 30FR and left front loudspeaker 58FL.

Further, when switching to the concentration mode, for example, controller 112 drives all right front loudspeaker 30FR, right rear loudspeaker 30RR, left front loudspeaker 58FL, and left rear loudspeaker 58RL. In this case, a sound signal for noise cancellation, which is stored in a memory (not shown) of acoustic device 2, is input to controller 112. Accordingly, controller 112 performs processing on the input sound signal to cause voice for the noise cancellation to be output from each of right front loudspeaker 30FR, right rear loudspeaker 30RR, left front loudspeaker 58FL, and left rear loudspeaker 58RL.

Further, when switching to the relax mode, for example, controller 112 drives all right front loudspeaker 30FR, right rear loudspeaker 30RR, left front loudspeaker 58FL, and left rear loudspeaker 58RL. In this case, a sound signal indicating an environmental sound (for example, chirping of birds, sound of waves, and the like), which is stored in a memory of acoustic device 2, is input to controller 112. Accordingly, controller 112 performs processing of adding a reflected sound or a reverberant sound to the input sound signal, thereby causing each of right front loudspeaker 30FR, right rear loudspeaker 30RR, left front loudspeaker 58FL, and left rear loudspeaker 58RL to output the environmental sound.

Furthermore, when receiving the action schedule data from action schedule data obtainer 110, controller 112 switches to a mode corresponding to the action schedule data from the plurality of modes described above. For example, when the action schedule data indicates an action schedule of "a web conference from 13:00 to 14:00 on May 31, 2021", controller 112 switches to the conference mode corresponding to the action schedule data from the plurality of modes at the date and time indicated by the action schedule data (at 13:00 on May 31, 2021). Accordingly, it is possible to automatically switch to the conference mode on the date and time of the web conference.

[1-3. Usage Example of Acoustic Device]

A usage example of acoustic device 2 according to Embodiment 1 will be described with reference to FIG. 3. Hereinafter, a case in which user 12 sits on seat 22 and conducts an online conference (web conference) will be described.

As shown in FIG. 3, terminal device 111 that can be connected to the Internet, microphone 113 that is connected to terminal device 111, and acoustic device 2 are used in the online conference. Terminal device 111 and microphone 113 are arranged on table 109 in front of seat 22. Acoustic device 2 is provided in a vicinity of head 14 of user 12 seated on seat 22. Further, when acceptor 108 of acoustic device 2 accepts an operation of selecting the conference mode by user 12, controller 112 switches to the conference mode from the plurality of modes.

Voice uttered by user 12 is picked up by microphone 113 placed on table 109 and delivered to the other party of the online conference. At this time, a part of the voice uttered by user 12 is absorbed by each of third sound absorbing modules 84 and 86. With this configuration, it is possible to prevent the voice uttered by user 12 from leaking to the surroundings.

Voice uttered by the other party of the online conference is output from right front loudspeaker 30FR and left front loudspeaker 58FL of acoustic device 2 and delivered to user 12. At this time, noise around user 12 is absorbed by first sound absorbing module 28 and second sound absorbing module 56. Accordingly, it is possible to prevent ambient noise from entering the ears of user 12.

[1-4. Effects]

In the present embodiment, as described above, first acoustic unit 6, second acoustic unit 8, and third acoustic unit 10 are arranged to respectively correspond to right-side head part 14*a*, left-side head part 14*b*, and back-side head part 14*c*, of user 12 seated on seat 22. With this configuration, a part of the voice uttered by user 12 is absorbed by third sound absorbing modules 84 and 86, so that the voice uttered by user 12 can be prevented from leaking to the surroundings. As a result, it is possible to prevent people around the user from feeling that the voice uttered by user 12 is annoying.

In addition, since the noise around user 12 is absorbed by first sound absorbing module 28 and second sound absorbing module 56, it is possible to prevent the noise around user 12 from entering the ears of user 12. Accordingly, user 12 can easily hear the sound output from each of first loudspeaker module 30 and second loudspeaker module 58 even with a volume at a low level. In this regard, even if the volume of each of first loudspeaker module 30 and second loudspeaker module 58 is reduced, user 12 can easily hear the sound output from each of first loudspeaker module 30 and second loudspeaker module 58. This makes it possible to prevent the leakage of the voice to the surroundings. As a result, it is possible to prevent people around the user from feeling that the sound output from each of first loudspeaker module 30 and second loudspeaker module 58 is annoying.

Embodiment 2

[2-1. Configuration of Acoustic Device]

Figure 13:
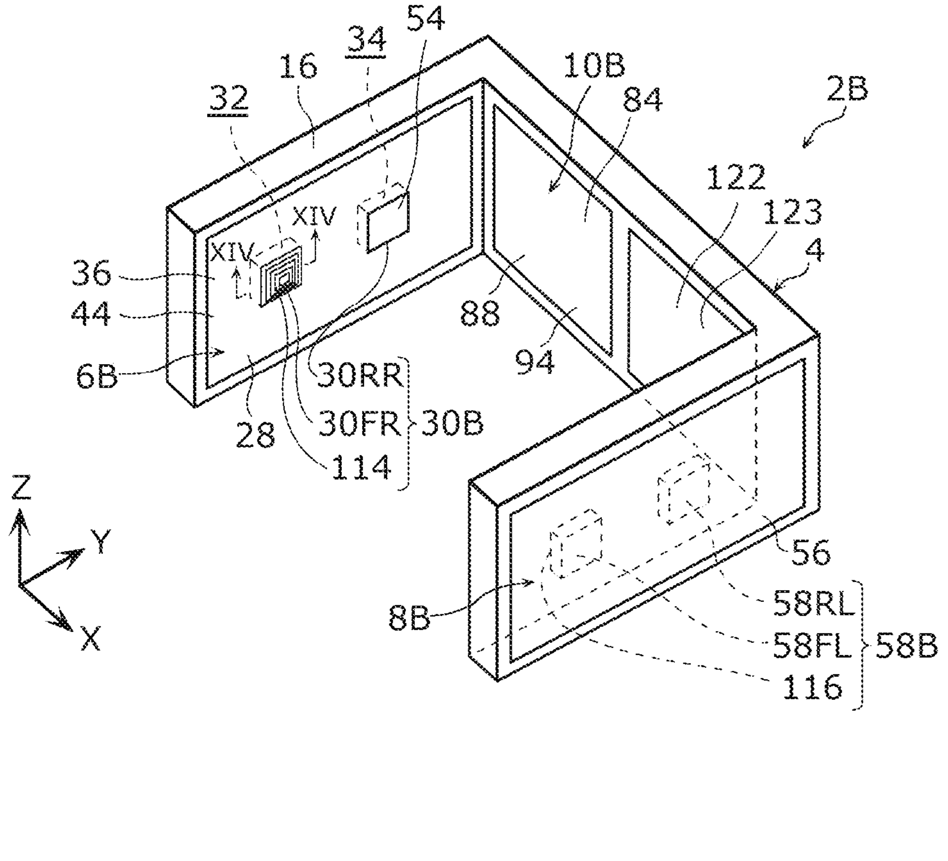
FIG. 13 is a perspective view showing an acoustic device according to Embodiment 2.
Figure 14:
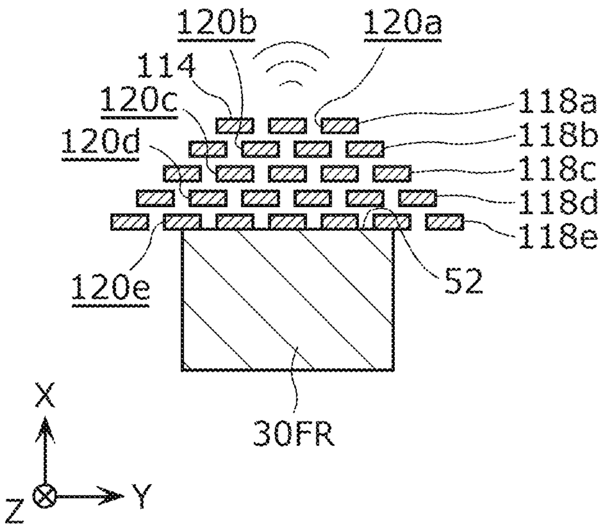
FIG. 14 is a cross-sectional view of an acoustic lens according to Embodiment 2, taken along the line XIV-XIV in FIG. 13.

A configuration of acoustic device 2B according to Embodiment 2 will be described with reference to FIGS. 13 and 14. FIG. 13 is a perspective view showing acoustic device 2B according to Embodiment 2. FIG. 14 is a cross-sectional view of acoustic lens 114 according to Embodiment 2, taken along line XIV-XIV in FIG. 13. It should be noted that the components same as those in Embodiment 1 are denoted by the same reference numerals, and descriptions of those components are omitted.

As shown in FIG. 13, in acoustic device 2B according to Embodiment 2, a pair of first loudspeaker modules 30B of first acoustic unit 6B includes: a) a combination of right front loudspeaker 30FR (an example of the first loudspeaker) and acoustic lens 114 (an example of a first directivity control member), and b) right rear loudspeaker 30RR.

In addition, a pair of second loudspeaker modules 58B of second acoustic unit 8B includes c) a combination of a left front loudspeaker 58FL (an example of the second loudspeaker) and acoustic lens 116 (an example of a second directivity control member), and d) left rear loudspeaker 58RL.

Acoustic lens 114 is arranged to face first sound emitting surface 52 (see FIG. 14) of right front loudspeaker 30FR, and controls the directivity of sound output from first sound emitting surface 52. Acoustic lens 114 causes the sound output from first sound emitting surface 52 of right front loudspeaker 30FR to be collected at or near the right ear of user 12 (see FIG. 3).

Acoustic lens 116 is arranged to face second sound emitting surface (not shown) of left front loudspeaker 30FR, and controls the directivity of sound output from second sound emitting surface. Acoustic lens 116 causes the sound output from second sound emitting surface of left front loudspeaker 58FL to be collected at or near the left ear of user 12.

Since the configurations of acoustic lenses 114 and 116 are the same, only the configuration of acoustic lens 114 will be described below. As shown in FIG. 14, acoustic lens 114 has a plurality of fins 118*a*, 118*b*, 118*c*, 118*d*, and 118*e* (118*a* to 118*e*). A plurality of fins 118*a* to 118*e* are each formed in a rectangular and thin plate shape and have the respective sizes different from one another. A plurality of fins 118*a* to 118*e* are spaced apart in this order in a direction along the thickness of acoustic lens 114 (X-axis direction). A size of fin 118*b* is larger than a size of fin 118*a*, a size of fin 118*c* is larger than the size of fin 118*b*, a size of fin 118*d* is larger than the size of fin 118*c*, and a size of fin 118*e* is larger than the size of fin 118*d*.

In addition, fin 118*a* has a plurality of holes 120*a* formed therein. Similarly, fin 118*b* has a plurality of holes 120*b* formed therein, fin 118*c* has a plurality of holes 120*c* formed therein, fin 118*d* has a plurality of holes 120*d* formed therein, and fin 118*e* has a plurality of holes 120*e* formed therein.

Although first loudspeaker module 30B includes acoustic lens 114 in the present embodiment, a horn (an example of the first directivity control member) for controlling the directivity of sound output from first sound emitting surface 52 may be included, instead of acoustic lens 114. Similarly, although second loudspeaker module 58B includes acoustic lens 116 in the present embodiment, a horn (an example of the second directivity control member) for controlling the directivity of sound output from the second sound emitting surface may be included, instead of acoustic lens 116.

Furthermore, as shown in FIG. 13, in acoustic device 2B according to Embodiment 2, third acoustic unit 10B has third sound absorbing module 84 and third loudspeaker module 122. Third loudspeaker module 122 is a woofer, and its reproduction band is a low sound range, which is an audible range that humans can recognize. Third loudspeaker module 122 has third sound emitting surface 123 arranged to face space 92 (see FIG. 4). Third sound absorbing surface 94 of third sound absorbing module 84 is arranged around third sound emitting surface 123 of third loudspeaker module 122 (more specifically, adjacent to third sound emitting surface 123).

[2-2. Functional Configuration of Acoustic Device]

Figure 15:
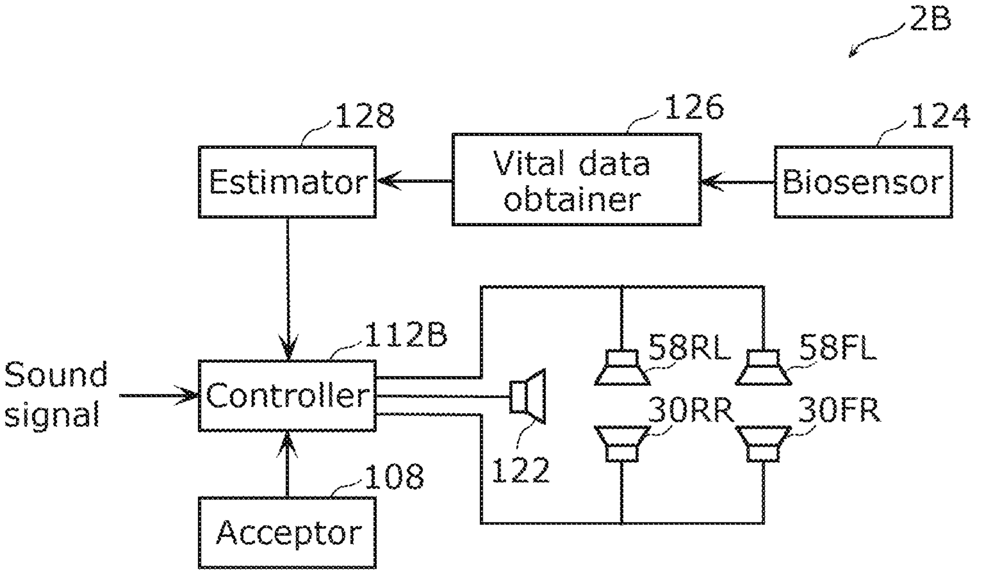
FIG. 15 is a block diagram showing a functional configuration of the acoustic device according to Embodiment 2.

Subsequently, a functional configuration of acoustic device 2B according to Embodiment 2 will be described with reference to FIG. 15. FIG. 15 is a block diagram showing the functional configuration of acoustic device 2B according to Embodiment 2.

As shown in FIG. 15, acoustic device 2B according to Embodiment 2 includes, as the functional configuration, biosensor 124, vital data obtainer 126, and estimator 128, instead of action schedule data obtainer 110 described in Embodiment 1 above.

Biosensor 124 is a sensor for detecting vital data of user 12 seated on seat 22 (see FIG. 3). The vital data is, for example, a heart rate, a brain wave, a respiration rate, a skin temperature, the number of blinks, and the like.

Vital data obtainer 126 obtains the vital data of user 12 from biosensor 124 and outputs the obtained vital data to estimator 128.

Estimator 128 estimates the condition of user 12 based on the vital data obtained by vital data obtainer 126. Estimator 128 outputs an estimation result to controller 112B.

For example, estimator 128 estimates that the condition of user 12 is a "concentrated condition", when a heart rate (bpm) that is vital data exceeds a threshold value. Furthermore, estimator 128 estimates that user 12 is in a "relaxed condition", when the heart rate (bpm) that is the vital data is equal to or less than the threshold value, for example.

For example, estimator 128 estimates that user 12 is in the "relaxed condition", when the brain wave that is the vital data is an $\alpha$ wave. Further, estimator 128 estimates that the condition of user 12 is the "concentrated condition", when the brain wave that is the vital data is a $\beta$ wave, for example.

Controller 112B performs processing on the input sound signal to control sound output from each of right front loudspeaker 30FR, right rear loudspeaker 30RR, left front loudspeaker 58FL, left rear loudspeaker 58RL, and third loudspeaker module 122.

Controller 112B also switches to a mode corresponding to the condition of user 12, which is estimated by estimator 128, from the plurality of modes (conference mode, concentration mode, and relax mode) described in Embodiment 1.

For example, when the condition of user 12, which is estimated by estimator 128, is the "concentrated condition", controller 112B switches to the conference mode or the concentration mode from the plurality of modes. Further, for example, when the condition of user 12, which is estimated by estimator 128, is the "relaxed condition", controller 112B switches to the relax mode from the plurality of modes.

Accordingly, it is possible to automatically switch to an optimum mode from the plurality of modes according to the condition of user 12.

[2-3. Effects]

In the present embodiment, the same effect as in Embodiment 1 can also be obtained.

(Other Verifications)

As described above, the acoustic device according to one or more aspects has been described based on the above embodiments, but the present disclosure is not limited to the above embodiments. An embodiment obtained by applying various modifications that are conceivable by a person skilled in the art to the embodiment, and an embodiment constructed by combining components of different embodiments may also be included in the scope of the one or more aspects, as long as these embodiments do not deviate from the spirit of the present disclosure.

Although acoustic device 2 (2B) is a headrest type acoustic device in each of the above embodiments, acoustic device 2 (2B) is not limited to the type, and may be a helmet type acoustic device that covers the head of user 12, for example.

Each of the elements in each of the above-described embodiments may be configured in the form of an exclusive hardware product, or may be realized by executing a software program suitable for the element. Each of the elements may be realized by means of a program executing unit, such as a central processing unit (CPU) and a processor, reading and executing the software program recorded on a recording medium such as a hard disk or a semiconductor memory.

A part or all of the functions of the acoustic device according to the above embodiments may be embodied by a processor such as a CPU executing a program.

A part or all of the components constituting each device described above may be configured by an integral circuit (IC) card or a single module, which can be attached to and detached from each device. The IC card or module is a computer system that includes a microprocessor, a read only memory (ROM), a random access memory (RAM), and the like. The IC card or module may include the super multifunctional LSI chip described above. The microprocessor operates according to the computer program, thereby allowing the IC card or module to achieve its function. This IC card or module may be tamper resistant.

The present disclosure may also be the methods described above. Furthermore, the present disclosure may be a computer program that embodies these methods by means of a computer, or may be a digital signal composed of the computer program. In addition, the present disclosure may be such that the computer program or the digital signal is recorded on a non-transitory computer-readable recording medium such as a flexible disc, a hard disk, a compact disc (CD)-ROM, a magneto-optical (MO) disc, a digital versatile disc (DVD), a DVD-ROM, a DVD-RAM, a Blu-ray (BD (registered trademark)) disc, a semiconductor memory, or the like. Alternatively, the present disclosure may be a digital signal recorded on these recording media. Further, the present disclosure may transmit the computer program or the digital signal via a telecommunication line, a wireless or wired communication line, a network typified by the Internet, data broadcasting, and the like. The present disclosure may also be a computer system provided with a microprocessor and a memory. The memory may store the computer program, and the microprocessor may operate in accordance with the computer program. In addition, the program or the digital signal may be recorded on the recording medium and transferred, or the program or the digital signal may be transferred via the network or the like, to thereby be embodied by another independent computer system.

INDUSTRIAL APPLICABILITY

An acoustic device according to the present disclosure is useful for a headrest-type acoustic device provided in a vicinity of the head of a user, for example.

The invention claimed is:

1. An acoustic device that is provided in a vicinity of a head of a user, the acoustic device comprising:

a first acoustic unit provided to face a right side of the head of the user;

a second acoustic unit provided to face a left side of the head of the user; and a third acoustic unit provided to face a back side of the head of the user, wherein the first acoustic unit includes:

a first loudspeaker module that includes a first sound emitting surface provided to face the second acoustic unit; and a first sound absorbing module that includes: a first sound absorbing surface that has a plurality of holes and is provided around the first sound emitting surface to face the second acoustic unit; and a Helmholtz resonator, the second acoustic unit includes:

a second loudspeaker module that includes a second sound emitting surface provided to face the first acoustic unit; and a second sound absorbing module that includes: a second sound absorbing surface that has a plurality of holes and is provided around the second sound emitting surface to face the first acoustic unit; and a Helmholtz resonator, the third acoustic unit includes:

a third sound absorbing module that includes a third sound absorbing surface provided to face a space between the first acoustic unit and the second acoustic unit; and a third loudspeaker module that includes a third sound emitting surface provided to face the space, the third sound absorbing surface of the third sound absorbing module is provided to be adjacent, in a left-right direction, to the third sound emitting surface of the third loudspeaker module, each of the first sound absorbing module and the second sound absorbing module includes a plurality of spaces arranged in a thickness direction from a side on which the first sound absorbing surface or the second sound absorbing surface is formed, the plurality of spaces communicate with each other, and lengths, in the thickness direction, of respective ones of a pair of adjacent spaces among the plurality of spaces are different from each other.

2. The acoustic device according to claim 1, wherein each of the first sound absorbing module and the second sound absorbing module is a sound absorbing element that absorbs sound with one or more sound absorption frequencies, and each of the first sound absorbing module and the second sound absorbing module includes one or a plurality of resonant spaces.

3. The acoustic device according to claim 1, wherein the first acoustic unit includes a plurality of first loudspeaker modules each being the first loudspeaker module, and the second acoustic unit includes a plurality of second loudspeaker modules each being the second loudspeaker module.

4. The acoustic device according to claim 1, wherein the first loudspeaker module includes:

a first loudspeaker that includes the first sound emitting surface; and a first directivity control member provided to face the first sound emitting surface of the first loudspeaker, for controlling directivity of sound output from the first sound emitting surface, and the second loudspeaker module includes:

a second loudspeaker that includes the second sound emitting surface; and a second directivity control member provided to face the second sound emitting surface of the second loudspeaker, for controlling directivity of sound output from the second sound emitting surface.

5. The acoustic device according to claim 4, wherein each of the first directivity control member and the second directivity control member is an acoustic lens or a horn.

6. The acoustic device according to claim 1, wherein a reproduction band of the first loudspeaker module is (i) an audible sound range that is humanly recognizable, the audible sound range being a low sound range or a medium-high sound range, or (ii) a non-audible sound range that is not humanly recognizable, and a reproduction band of the second loudspeaker module is (i) an audible sound range that is humanly recognizable, the audible sound range being a low sound range or a medium-high sound range, or (ii) a non-audible sound range that is not humanly recognizable.

7. The acoustic device according to claim 1, wherein the first sound emitting surface of the first loudspeaker module and the first sound absorbing surface of the first sound absorbing module are arranged substantially parallel to each other, and the second sound emitting surface of the second loudspeaker module and the second sound absorbing surface of the second sound absorbing module are arranged substantially parallel to each other.

8. The acoustic device according to claim 1, further comprising:

a controller that switches to one mode among a plurality of modes having mutually different acoustic characteristics, and controls sound output from each of the first loudspeaker module and the second loudspeaker module, according to the one mode switched to.

9. The acoustic device according to claim 8, further comprising:

an action schedule data obtainer that obtains action schedule data indicating an action schedule of the user, wherein the controller switches to, among the plurality of modes, a mode corresponding to the action schedule data obtained by the action schedule data obtainer.

10. The acoustic device according to claim 8, further comprising:

a vital data obtainer that obtains vital data of the user; and an estimator that estimates a condition of the user based on the vital data obtained by the vital data obtainer, wherein the controller switches to, among the plurality of modes, a mode corresponding to the condition of the user estimated by the estimator.

11. The acoustic device according to claim 1, wherein the third sound absorbing surface has a plurality of holes, and the third sound absorbing module includes a Helmholtz resonator that includes one or a plurality of resonant spaces.

12. An acoustic device that is provided in a vicinity of a head of a user, the acoustic device comprising:

a first acoustic unit provided to face a right side of the head of the user;

a second acoustic unit provided to face a left side of the head of the user; and a third acoustic unit provided to face a back side of the head of the user, wherein the first acoustic unit includes:

a first loudspeaker module that includes a first sound emitting surface provided to face the second acoustic unit; and a first sound absorbing module that includes a first sound absorbing surface provided around the first sound emitting surface to face the second acoustic unit, the second acoustic unit includes:

a second loudspeaker module that includes a second sound emitting surface provided to face the first acoustic unit; and a second sound absorbing module that includes a second sound absorbing surface provided around the second sound emitting surface to face the first acoustic unit, the third acoustic unit includes:

a third sound absorbing module that includes a third sound absorbing surface provided to face a space between the first acoustic unit and the second acoustic unit; and a third loudspeaker module that includes a third sound emitting surface provided to face the space, the third sound absorbing surface of the third sound absorbing module is provided to be adjacent, in a left-right direction, to the third sound emitting surface of the third loudspeaker module, the first loudspeaker module includes:

a first loudspeaker that includes the first sound emitting surface; and a first directivity control member provided to face the first sound emitting surface of the first loudspeaker, for controlling directivity of sound output from the first sound emitting surface, the second loudspeaker module includes:

a second loudspeaker that includes the second sound emitting surface; and a second directivity control member provided to face the second sound emitting surface of the second loudspeaker, for controlling directivity of sound output from the second sound emitting surface, each of the first directivity control member and the second directivity control member is an acoustic lens or a horn, each of the first sound absorbing module and the second sound absorbing module includes a plurality of spaces arranged in a thickness direction from a side on which the first sound absorbing surface or the second sound absorbing surface is formed, the plurality of spaces communicate with each other, and lengths, in the thickness direction, of respective ones of a pair of adjacent spaces among the plurality of spaces are different from each other.

* * * * *